(12) United States Patent
Luoma

(10) Patent No.: US 10,379,130 B2
(45) Date of Patent: Aug. 13, 2019

(54) REACTION VESSEL EXCHANGER DEVICE FOR A DIAGNOSTIC ANALYZER

(71) Applicant: Abbott Laboratories, Abbott Park, IL (US)

(72) Inventor: Robert Luoma, Colleyville, TX (US)

(73) Assignee: ABBOTT LABORATORIES, Abbott Park, IL (US)

( * ) Notice: Subject to any disclaimer, the term of this patent is extended or adjusted under 35 U.S.C. 154(b) by 27 days.

(21) Appl. No.: 15/193,990

(22) Filed: Jun. 27, 2016

(65) Prior Publication Data

US 2016/0377642 A1 Dec. 29, 2016

Related U.S. Application Data

(60) Provisional application No. 62/185,541, filed on Jun. 26, 2015.

(51) Int. Cl.
| | |
|---|---|
| *G01N 35/04* | (2006.01) |
| *G01N 35/02* | (2006.01) |
| *G01N 35/10* | (2006.01) |
| *G01N 35/00* | (2006.01) |

(52) U.S. Cl.
CPC ........... *G01N 35/04* (2013.01); *G01N 35/025* (2013.01); *G01N 35/1002* (2013.01); *G01N 2035/00356* (2013.01); *G01N 2035/0427* (2013.01); *G01N 2035/0443* (2013.01); *G01N 2035/0465* (2013.01); *G01N 2035/0472* (2013.01)

(58) Field of Classification Search
None
See application file for complete search history.

(56) References Cited

U.S. PATENT DOCUMENTS

| | | | |
|---|---|---|---|
| 3,617,222 | A | 11/1971 | Matte |
| 3,854,879 | A | 12/1974 | Figueroa et al. |
| 3,883,305 | A | 5/1975 | Hoskins et al. |
| 4,039,287 | A | 8/1977 | Moran |

(Continued)

FOREIGN PATENT DOCUMENTS

| | | |
|---|---|---|
| CN | 1099084 | 5/1998 |
| CN | 1181826 | 5/1998 |

(Continued)

OTHER PUBLICATIONS

International Search Report for PCT/US16/39581 dated Nov. 3, 2016, 16 pages.

(Continued)

*Primary Examiner* — Kathryn Wright
(74) *Attorney, Agent, or Firm* — Klintworth & Rozenblat IP LLP

(57) ABSTRACT

A diagnostic analyzer includes a first sample process path, a second sample processing path, and a reaction vessel exchanger device. The first sample process path includes an incubation track operable to move reaction vessels along the first sample process path. The second sample process path includes a processing track, disposed below the first sample process path, which is operable to move reaction vessels along the second sample process path. The reaction vessel exchanger device is configured to transfer the reaction vessels from the first sample processing path to the second sample processing path.

8 Claims, 12 Drawing Sheets

(56) References Cited

U.S. PATENT DOCUMENTS

| | | |
|---|---|---|
| 4,039,288 A | 8/1977 | Moran |
| 4,287,155 A | 9/1981 | Tersteeg et al. |
| 4,315,891 A | 2/1982 | Sakurada |
| 4,528,159 A | 7/1985 | Liston |
| 4,753,775 A | 6/1988 | Ebersole et al. |
| 4,767,716 A | 8/1988 | Sakamaki et al. |
| 4,952,518 A | 8/1990 | Johnson et al. |
| 5,008,082 A | 4/1991 | Shaw |
| 5,057,823 A | 10/1991 | Dyer et al. |
| 5,063,790 A | 11/1991 | Freeman et al. |
| 5,071,625 A | 12/1991 | Kelln et al. |
| 5,075,079 A | 12/1991 | Kerr et al. |
| 5,077,013 A | 12/1991 | Guigan |
| 5,084,242 A | 1/1992 | Sakuma et al. |
| 5,089,229 A | 2/1992 | Heidt et al. |
| 5,104,621 A | 4/1992 | Pfost et al. |
| 5,104,808 A | 4/1992 | Laska et al. |
| 5,108,703 A | 4/1992 | Pfost et al. |
| 5,125,748 A | 6/1992 | Bjornson et al. |
| 5,128,105 A | 7/1992 | Berthold et al. |
| 5,137,693 A | 8/1992 | Mawhirt |
| 5,139,744 A | 8/1992 | Kowalski |
| 5,141,871 A | 8/1992 | Kureshy |
| 5,158,748 A | 10/1992 | Obi |
| 5,158,895 A | 10/1992 | Ashiara |
| 5,167,926 A | 12/1992 | Kimura |
| 5,173,741 A | 12/1992 | Wakatake |
| 5,178,834 A | 1/1993 | Kagayama et al. |
| 5,192,506 A | 3/1993 | Kureshy |
| 5,240,678 A | 8/1993 | Rochester |
| 5,246,665 A | 9/1993 | Tyranski |
| 5,294,404 A | 3/1994 | Grandone |
| 5,306,510 A | 4/1994 | Meltzer |
| 5,340,544 A | 8/1994 | Nishikawa |
| 5,351,801 A | 10/1994 | Markin et al. |
| 5,366,697 A | 11/1994 | Tomasso |
| 5,374,395 A | 12/1994 | Robinson |
| 5,380,666 A | 1/1995 | Wuerschum |
| 5,402,875 A | 4/1995 | Markin et al. |
| 5,411,065 A | 5/1995 | Meador |
| 5,424,036 A | 6/1995 | Ushikubo |
| 5,441,891 A | 8/1995 | Burkovich |
| 5,443,791 A | 8/1995 | Cathcart |
| 5,455,006 A | 10/1995 | Aota |
| 5,462,715 A | 10/1995 | Koch et al. |
| 5,482,861 A | 1/1996 | Clark |
| 5,501,838 A | 3/1996 | Ootani |
| 5,567,386 A | 10/1996 | Markin |
| 5,582,796 A * | 12/1996 | Carey .................... B01L 3/508 198/393 |
| 5,585,068 A | 12/1996 | Panetz |
| 5,605,665 A | 2/1997 | Clark |
| 5,610,069 A | 3/1997 | Clark |
| 5,623,415 A | 4/1997 | O'Bryan |
| 5,635,364 A | 6/1997 | Clark |
| 5,637,275 A | 6/1997 | Carey |
| 5,645,800 A | 7/1997 | Masterson |
| 5,658,532 A | 8/1997 | Kurosaki et al. |
| 5,663,545 A | 9/1997 | Marquiss |
| 5,670,375 A | 9/1997 | Seaton |
| 5,714,127 A | 2/1998 | Dewitt |
| 5,720,377 A | 2/1998 | Lapeus |
| 5,735,387 A | 4/1998 | Polaniec |
| 5,736,102 A | 4/1998 | Seaton |
| 5,741,708 A | 4/1998 | Carey |
| 5,762,873 A | 6/1998 | Fanning |
| 5,762,874 A | 6/1998 | Seaton |
| 5,762,878 A | 6/1998 | Clark |
| 5,798,084 A | 8/1998 | Seaton |
| 5,798,085 A | 8/1998 | Seaton |
| 5,855,847 A | 1/1999 | Oonuma |
| 5,856,193 A | 1/1999 | Fanning |
| 5,895,628 A | 4/1999 | Heid et al. |
| 5,897,835 A | 4/1999 | Seaton |
| 5,965,090 A | 10/1999 | Fanning |
| 5,972,721 A | 10/1999 | Bruno |
| 6,006,800 A | 12/1999 | Nakano |
| 6,086,824 A | 7/2000 | Fanning |
| 6,098,819 A | 8/2000 | Hamburg |
| 6,102,984 A | 8/2000 | Carl |
| 6,111,930 A | 8/2000 | Schipper |
| 6,190,617 B1 | 2/2001 | Clark |
| 6,202,829 B1 | 3/2001 | van Dyke, Jr. et al. |
| 6,207,031 B1 | 3/2001 | Adourian |
| 6,245,297 B1 | 6/2001 | Kowallis |
| 6,325,114 B1 | 12/2001 | Bevirt |
| 6,358,470 B1 | 3/2002 | Higuchi |
| 6,358,471 B1 | 3/2002 | Ishihara |
| 6,368,872 B1 | 4/2002 | Juranas |
| 6,372,185 B1 | 4/2002 | Shumate |
| 6,432,365 B1 | 8/2002 | Levin |
| 6,436,292 B1 | 8/2002 | Petro |
| 6,436,349 B1 | 8/2002 | Carey |
| 6,458,533 B1 | 10/2002 | Felder |
| 6,461,570 B2 | 10/2002 | Ishihara |
| 6,498,037 B1 | 12/2002 | Carey |
| 6,503,457 B1 | 1/2003 | Neeper |
| 6,551,833 B1 | 4/2003 | Lehtinen |
| 6,566,143 B2 | 5/2003 | Hoyt |
| 6,656,428 B1 | 12/2003 | Clark |
| 6,669,432 B2 | 12/2003 | Hudson |
| 6,678,577 B1 | 1/2004 | Stylli |
| 6,694,128 B1 | 2/2004 | Sorrells et al. |
| 6,780,648 B1 | 8/2004 | Sun |
| 6,803,239 B2 | 10/2004 | McLean |
| 6,808,935 B2 | 10/2004 | Levin |
| 6,866,820 B1 | 3/2005 | Otto et al. |
| 6,919,044 B1 | 7/2005 | Shibata |
| 7,101,510 B2 | 9/2006 | Vann |
| 7,159,740 B2 | 1/2007 | Nunthakumar et al. |
| 7,182,912 B2 | 2/2007 | Carey |
| 7,217,392 B2 | 5/2007 | Bogen |
| 7,335,338 B2 | 2/2008 | Schermer |
| 7,361,309 B2 | 4/2008 | Vann |
| 7,371,347 B2 | 5/2008 | Wulf |
| 7,435,383 B2 | 10/2008 | Tseung |
| 7,501,094 B2 | 3/2009 | Bysouth |
| 7,514,046 B2 | 4/2009 | Kechagia |
| 7,585,463 B2 | 9/2009 | Austin |
| 7,597,847 B2 | 10/2009 | Tomasso et al. |
| 7,608,466 B2 | 10/2009 | Hornauer |
| 7,611,905 B2 | 11/2009 | Kunuki |
| 7,628,954 B2 | 12/2009 | Gomm |
| 7,670,553 B2 | 3/2010 | Babson |
| 7,681,466 B2 | 3/2010 | Miller |
| 7,713,708 B2 | 5/2010 | Roback |
| 7,718,435 B1 | 5/2010 | Bogen |
| 7,718,442 B2 | 5/2010 | Davis |
| 7,785,534 B2 | 8/2010 | Watari |
| 7,790,462 B2 | 9/2010 | Fournier |
| 7,815,866 B2 | 10/2010 | Safar |
| 7,841,824 B2 | 11/2010 | Zobel et al. |
| 7,846,384 B2 | 12/2010 | Watson et al. |
| 7,854,892 B2 | 12/2010 | Veiner |
| 7,910,065 B2 | 3/2011 | Clark |
| 7,921,989 B2 | 4/2011 | Itoh |
| 7,959,875 B2 | 6/2011 | Zhou |
| 7,980,119 B2 | 7/2011 | Maeda et al. |
| 7,985,375 B2 | 7/2011 | Edens et al. |
| 7,987,736 B2 | 8/2011 | Rapaud |
| 7,998,751 B2 | 8/2011 | Evers et al. |
| 8,007,740 B2 | 8/2011 | Liu et al. |
| 8,008,066 B2 | 8/2011 | Lair |
| 8,021,611 B2 | 9/2011 | Roach |
| 8,038,942 B2 | 10/2011 | Ping |
| 8,057,756 B2 | 11/2011 | Londo et al. |
| 8,114,349 B2 | 2/2012 | Amirkhanian |
| 8,124,028 B2 | 2/2012 | Fulton |
| 8,142,739 B2 | 3/2012 | Tseung |
| 8,158,059 B2 | 4/2012 | Kennedy et al. |
| 8,158,061 B2 | 4/2012 | Shah et al. |
| 8,182,745 B2 | 5/2012 | Chiba et al. |
| 8,182,761 B2 | 5/2012 | Nakagawa |
| 8,211,381 B2 | 7/2012 | Ricci et al. |

(56) References Cited

U.S. PATENT DOCUMENTS

| | | |
|---|---|---|
| 8,222,048 B2 | 7/2012 | Fritchie |
| 8,232,103 B2 | 7/2012 | Miller et al. |
| 8,257,650 B2 | 9/2012 | Chow |
| 8,266,973 B2 | 9/2012 | Maeda et al. |
| 8,277,729 B2 | 10/2012 | Matsuo |
| 8,277,752 B2 | 10/2012 | Nakagawa |
| 8,278,108 B2 | 10/2012 | Wada et al. |
| 8,287,820 B2 | 10/2012 | Williams |
| 8,293,175 B2 | 10/2012 | Hotlund |
| 8,348,370 B2 | 1/2013 | Peters |
| 8,361,387 B2 | 1/2013 | Schacher et al. |
| 8,367,022 B2 | 2/2013 | Warhurst et al. |
| 8,372,355 B2 | 2/2013 | Zhou |
| 8,377,377 B2 | 2/2013 | Angros |
| 8,377,394 B2 | 2/2013 | Sakowski |
| 8,383,421 B2 | 2/2013 | Yanagida |
| 8,389,297 B2 | 3/2013 | Pamula |
| 8,486,335 B2 | 7/2013 | Angros |
| 8,492,155 B2 | 7/2013 | Bunce |
| 8,501,461 B2 | 8/2013 | Knight et al. |
| 8,535,624 B2 | 9/2013 | Luoma |
| 8,545,756 B2 | 10/2013 | Hotlund |
| 8,549,934 B2 | 10/2013 | Biksacky |
| 8,551,421 B2 | 10/2013 | Luchinger |
| 8,574,511 B2 | 11/2013 | Nakagawa |
| 8,585,987 B2 | 11/2013 | Tseung |
| 8,586,347 B2 | 11/2013 | Lochhead |
| 8,616,072 B2 | 12/2013 | Boeke et al. |
| 8,641,970 B2 | 2/2014 | Chung et al. |
| 8,663,991 B2 | 3/2014 | Reinhardt |
| 8,679,421 B2 | 3/2014 | Sano et al. |
| 8,696,990 B2 | 4/2014 | Meller et al. |
| 8,715,593 B2 | 5/2014 | Brewer et al. |
| 8,718,948 B2 | 5/2014 | Heinz et al. |
| 8,747,745 B2 | 6/2014 | Kiataoka |
| 8,770,046 B2 | 7/2014 | Maeda et al. |
| 8,778,280 B2 | 7/2014 | zhou |
| 8,790,593 B2 | 7/2014 | Clark et al. |
| 8,800,747 B2 | 8/2014 | Pedrazzini |
| 8,804,114 B2 | 8/2014 | Ingber |
| 8,808,649 B2 | 8/2014 | Ingber |
| 8,809,069 B2 | 8/2014 | Brady et al. |
| 8,821,791 B2 | 9/2014 | Shibata et al. |
| 8,840,848 B2 | 9/2014 | Kraihanzel |
| 8,840,851 B2 | 9/2014 | Kowari et al. |
| 8,863,593 B2 | 10/2014 | Weng |
| 8,865,069 B2 | 10/2014 | Gut et al. |
| 8,877,128 B2 | 11/2014 | Fukugaki et al. |
| 8,956,570 B2 | 2/2015 | Wilson et al. |
| 8,968,655 B2 | 3/2015 | Champseix et al. |
| 8,973,736 B2 | 3/2015 | Johns et al. |
| 9,046,455 B2 | 6/2015 | Wilson et al. |
| 9,050,598 B2 | 6/2015 | Tsukioka |
| 9,103,807 B2 | 8/2015 | Kitagawa et al. |
| 9,110,043 B2 | 8/2015 | Kaneko |
| 9,134,332 B2 | 9/2015 | Frey et al. |
| 9,213,041 B2 | 12/2015 | Kitagawa et al. |
| 9,229,019 B2 | 1/2016 | Tokieda et al. |
| 9,233,804 B2 | 1/2016 | Pedrazzini |
| 9,248,980 B2 | 2/2016 | Pedrazzini |
| 9,248,982 B2 | 2/2016 | Eberhardt et al. |
| 9,267,957 B2 | 2/2016 | Haechler et al. |
| 9,285,383 B2 | 3/2016 | Toyoshima et al. |
| 9,291,633 B2 | 3/2016 | Ohga et al. |
| 9,316,659 B2 | 4/2016 | Dumitrescu |
| 9,335,338 B2 | 5/2016 | Ochranek et al. |
| 9,347,964 B2 | 5/2016 | Schacher |
| 2002/0055176 A1 | 5/2002 | Ray |
| 2002/0104389 A1 | 8/2002 | Hovey |
| 2002/0166592 A1 | 11/2002 | Liu et al. |
| 2004/0096368 A1 | 5/2004 | Davis et al. |
| 2004/0156748 A1 | 8/2004 | Yamakawa et al. |
| 2005/0003522 A1 | 1/2005 | Carlsen et al. |
| 2005/0085725 A1 | 4/2005 | Nagar et al. |
| 2005/0112783 A1 | 5/2005 | Evans et al. |
| 2006/0002820 A1 | 1/2006 | Baumann et al. |
| 2007/0092403 A1 | 4/2007 | Wirbisky et al. |
| 2007/0148701 A1 | 6/2007 | Roback et al. |
| 2007/0231217 A1 | 10/2007 | Clinton et al. |
| 2010/0144053 A1 | 6/2010 | Haushalter et al. |
| 2010/0180698 A1 | 7/2010 | Lopez Alvarez et al. |
| 2011/0076194 A1 | 3/2011 | Kitagawa et al. |
| 2011/0271773 A1 | 11/2011 | Komatsu et al. |
| 2011/0293475 A1* | 12/2011 | Rosenberg ........... G01N 35/025 422/64 |
| 2012/0048036 A1 | 3/2012 | Mimura et al. |
| 2012/0213667 A1 | 8/2012 | Roach et al. |
| 2012/0251389 A1 | 10/2012 | Akutsu |
| 2012/0258463 A1 | 10/2012 | Duffy et al. |
| 2012/0282603 A1 | 11/2012 | Hansen et al. |
| 2012/0282684 A1 | 11/2012 | Fritchie et al. |
| 2012/0309635 A1 | 12/2012 | Trinkle et al. |
| 2013/0017128 A1 | 1/2013 | Silbert et al. |
| 2013/0017535 A1 | 1/2013 | Frey et al. |
| 2013/0037564 A1 | 2/2013 | Williams et al. |
| 2013/0047751 A1 | 2/2013 | Voss et al. |
| 2013/0068041 A1 | 3/2013 | Naumann et al. |
| 2013/0078625 A1 | 3/2013 | Holmes et al. |
| 2013/0136670 A1 | 5/2013 | Wiltsie et al. |
| 2013/0142711 A1 | 6/2013 | Wilson et al. |
| 2013/0160533 A1 | 6/2013 | Fukuma et al. |
| 2013/0195720 A1 | 8/2013 | Behnk et al. |
| 2013/0203046 A1 | 8/2013 | Wiltsie |
| 2013/0209334 A1 | 8/2013 | Wilson et al. |
| 2013/0310964 A1 | 11/2013 | Yano et al. |
| 2014/0004548 A1 | 1/2014 | Gordon et al. |
| 2014/0039671 A1 | 2/2014 | Raghibizadeh et al. |
| 2014/0045210 A1 | 2/2014 | Menges et al. |
| 2014/0047931 A1 | 2/2014 | Mettier et al. |
| 2014/0106467 A1 | 4/2014 | Hutter et al. |
| 2014/0186238 A1 | 7/2014 | Holmes et al. |
| 2014/0273241 A1 | 9/2014 | Ochranek et al. |
| 2014/0273242 A1 | 9/2014 | Ochranek et al. |
| 2014/0287523 A1 | 9/2014 | Donohue |
| 2014/0295563 A1 | 10/2014 | Matsuura |
| 2014/0305227 A1 | 10/2014 | Johns |
| 2014/0308661 A1 | 10/2014 | Holmes et al. |
| 2014/0363259 A1 | 12/2014 | Lorenzen et al. |
| 2015/0064802 A1 | 3/2015 | Pollack et al. |
| 2015/0079684 A1 | 3/2015 | Bucher et al. |
| 2015/0147819 A1 | 5/2015 | Pedrazzini |
| 2015/0160249 A1 | 6/2015 | Bucher et al. |
| 2015/0166265 A1 | 6/2015 | Pollack et al. |
| 2015/0177267 A1 | 6/2015 | Oonuma et al. |
| 2015/0197362 A1 | 7/2015 | Sato |
| 2015/0233955 A1 | 8/2015 | Nemoto et al. |
| 2015/0260746 A1 | 9/2015 | Pedrazzini |
| 2015/0274423 A1 | 10/2015 | Borodkin et al. |
| 2015/0285829 A1 | 10/2015 | Rousseau |
| 2015/0316467 A1 | 11/2015 | Kaneko |
| 2015/0355211 A1 | 12/2015 | Mellars et al. |
| 2015/0369832 A1 | 12/2015 | Sacco |
| 2016/0025756 A1 | 1/2016 | Pollack et al. |
| 2016/0032358 A1 | 2/2016 | Buse et al. |
| 2016/0039615 A1 | 2/2016 | Otts |
| 2016/0083195 A1 | 3/2016 | Sachs |
| 2016/0084862 A1 | 3/2016 | Feingold et al. |
| 2016/0161520 A1 | 6/2016 | Pedrazzini |

FOREIGN PATENT DOCUMENTS

| | | |
|---|---|---|
| CN | 1712969 | 12/2005 |
| CN | 10156638 | 10/2009 |
| CN | 101925525 | 12/2010 |
| CN | 10223224 | 4/2011 |
| CN | 102472761 | 5/2012 |
| CN | 102472765 | 5/2012 |
| CN | 102608341 | 7/2012 |
| CN | 102621337 | 8/2012 |
| CN | 102822678 | 12/2012 |
| CN | 102879591 | 1/2013 |
| CN | 202735420 | 2/2013 |
| CN | 203053987 | 7/2013 |
| CN | 203630149 | 6/2014 |

(56) References Cited

FOREIGN PATENT DOCUMENTS

| | | |
|---|---|---|
| CN | 103975245 | 8/2014 |
| CN | 203786133 | 8/2014 |
| CN | 104040352 | 9/2014 |
| CN | 104040353 | 9/2014 |
| CN | 104040357 | 9/2014 |
| CN | 104053997 | 9/2014 |
| CN | 203825021 | 9/2014 |
| CN | 203825022 | 9/2014 |
| CN | 104105969 | 10/2014 |
| CN | 203941178 | 11/2014 |
| CN | 204008673 | 12/2014 |
| CN | 104569461 | 4/2015 |
| EP | 0260136 | 3/1988 |
| EP | 0467284 | 1/1992 |
| EP | 0629858 | 12/1994 |
| EP | 0 802 412 A2 | 10/1997 |
| EP | 0809829 | 12/1997 |
| EP | 0867724 | 9/1998 |
| EP | 0882500 | 12/1998 |
| EP | 1041386 | 10/2000 |
| EP | 1055926 A2 | 11/2000 |
| EP | 1240944 A2 | 9/2002 |
| EP | 1546737 | 2/2004 |
| EP | 1468289 A2 | 10/2004 |
| EP | 1087231 B1 | 11/2004 |
| EP | 1517147 A2 | 3/2005 |
| EP | 1507594 | 8/2006 |
| EP | 1700563 A2 | 9/2006 |
| EP | 1805517 A | 7/2007 |
| EP | 1867978 A1 | 12/2007 |
| EP | 1867997 A1 | 12/2007 |
| EP | 1873530 A1 | 1/2008 |
| EP | 1906186 A2 | 4/2008 |
| EP | 1767272 B1 | 3/2010 |
| EP | 1508613 B1 | 10/2010 |
| EP | 2288442 A2 | 3/2011 |
| EP | 2299281 | 3/2011 |
| EP | 2347011 A1 | 7/2011 |
| EP | 1639368 B1 | 10/2011 |
| EP | 2472267 | 7/2012 |
| EP | 1767271 B1 | 12/2012 |
| EP | 2720036 | 4/2014 |
| EP | 2902789 | 8/2015 |
| GB | 2397126 A | 7/2004 |
| GB | 2477053 A | 7/2011 |
| GB | 2502409 A | 11/2013 |
| GB | 2504241 A | 1/2014 |
| GB | 2507772 A | 5/2014 |
| JP | H04 9668 A | 1/1992 |
| JP | 2009264737 | 11/2009 |
| JP | 2013224970 | 10/2013 |
| WO | 09625712 | 8/1996 |
| WO | 200155727 A1 | 8/2001 |
| WO | 200227630 A1 | 4/2002 |
| WO | 2003027325 A2 | 4/2003 |
| WO | 2003036304 A1 | 5/2003 |
| WO | 2004003219 A2 | 1/2004 |
| WO | 2004003504 A2 | 1/2004 |
| WO | 2004099378 A2 | 11/2004 |
| WO | 2005003729 A2 | 1/2005 |
| WO | 2005016527 A2 | 2/2005 |
| WO | 2005085854 A1 | 9/2005 |
| WO | 2005100948 | 10/2005 |
| WO | 2006072033 A2 | 7/2006 |
| WO | 2006110725 A2 | 10/2006 |
| WO | 2007084425 A2 | 7/2007 |
| WO | 2008007280 A2 | 1/2008 |
| WO | 2008070676 A2 | 6/2008 |
| WO | 2008121239 A1 | 10/2008 |
| WO | 2009043050 A2 | 4/2009 |
| WO | 2009091410 A1 | 7/2009 |
| WO | 2009092710 | 7/2009 |
| WO | 2010036352 A1 | 4/2010 |
| WO | 2010056890 A1 | 5/2010 |
| WO | 2011017094 A2 | 2/2011 |
| WO | 2011036190 | 3/2011 |
| WO | 2011040196 | 4/2011 |
| WO | 2011040197 | 4/2011 |
| WO | 2011122607 | 10/2011 |
| WO | 2012009617 A2 | 1/2012 |
| WO | 2012012779 A2 | 1/2012 |
| WO | 2012106827 A1 | 8/2012 |
| WO | 2013169778 | 11/2013 |

OTHER PUBLICATIONS

International Preliminary Report on Patentability for PCT/US2016/039559, dated Dec. 26, 2017, 8 pages.
International Preliminary Report on Patentability for PCT/US2016/039581, dated Dec. 26, 2017, 8 pages.
Extended European Search Report for European Patent Application No. EP 16 81 5491 dated Dec. 17, 2018, 10 pages.

* cited by examiner

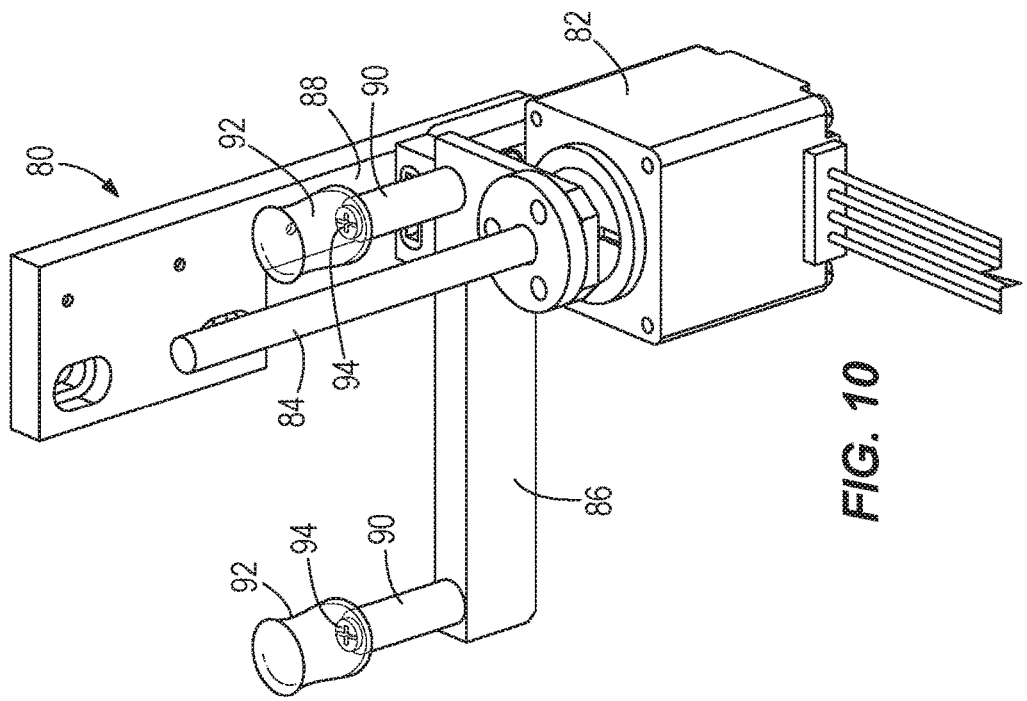
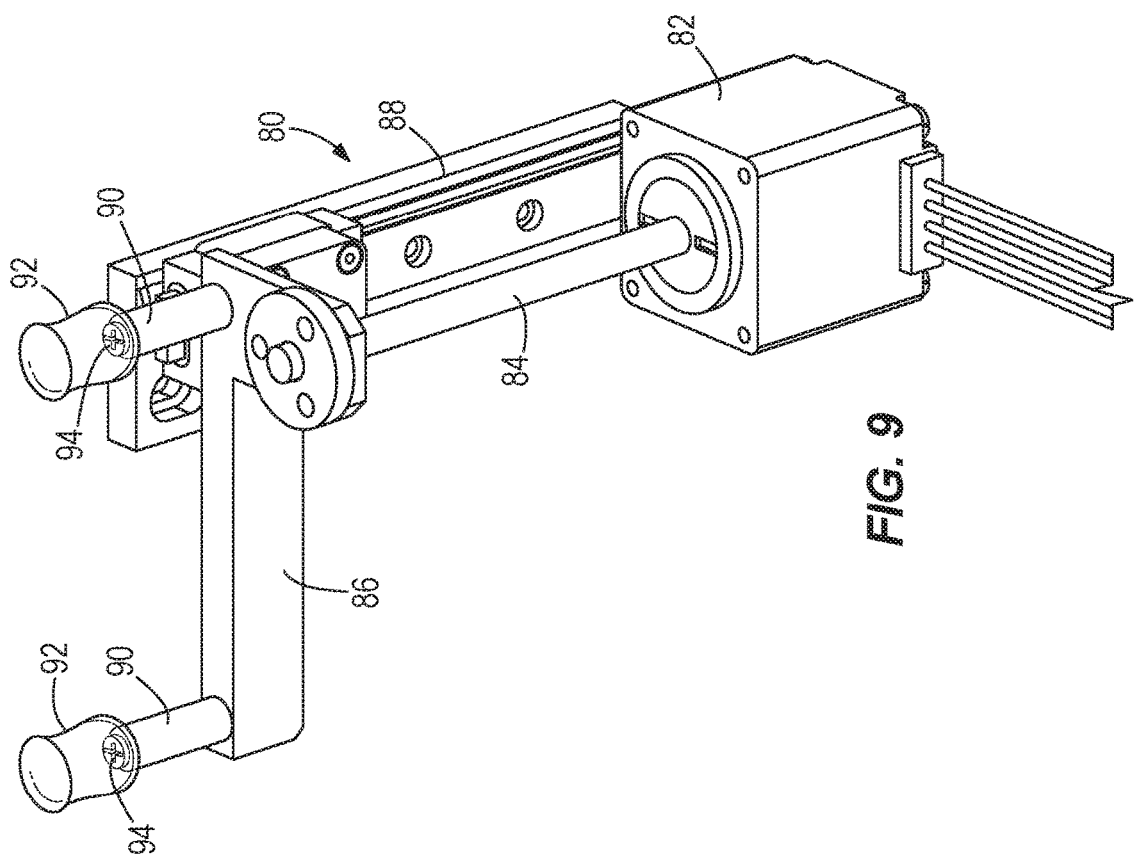

REACTION VESSEL EXCHANGER DEVICE FOR A DIAGNOSTIC ANALYZER

CROSS-REFERENCE TO RELATED APPLICATION

This application claims the benefit of U.S. Provisional Application No. 62/185,541 filed Jun. 26, 2015.

FIELD OF THE DISCLOSURE

This disclosure relates to a diagnostic analyzer having reactions on a plurality of proximate process paths and to a reaction vessel exchanger devices for transferring reaction vessels between process paths of a diagnostic analyzer.

BACKGROUND

Diagnostic analyzers are used to analyze samples in order to detect one or more conditions of the sample. In the past, diagnostic analyzers require multiple processing steps to be performed on a sample to perform an assay test. In some cases, the diagnostic analyzers are large and occupy significant floor space.

A diagnostic analyzer and method of use is needed to reduce or eliminate one or more issues experienced by one or more of the current diagnostic analyzers.

SUMMARY

In one embodiment, a diagnostic analyzer is disclosed. The diagnostic analyzer includes a first sample process path, a second sample processing path, and a reaction vessel exchanger device. The first sample process path includes an incubation track operable to move reaction vessels along the first sample process path. The second sample process path includes a processing track, disposed below the first sample process path, which is operable to move reaction vessels along the second sample process path. The reaction vessel exchanger device is configured to transfer the reaction vessels from the first sample processing path to the second sample processing path.

In another embodiment, a diagnostic analyzer is disclosed. The diagnostic analyzer includes an incubation track, at least one processing track, and a reaction vessel exchanger device. The incubation track is configured to move reaction vessels held by the incubation track. The at least one processing track is disposed below the incubation track in a non-parallel alignment. The reaction vessel exchanger device is configured to transfer the reaction vessels held by the incubation track to the at least one processing track. The incubation track includes a plurality of incubation track slots for holding the reaction vessels. The at least one processing track comprises a plurality of processing track slots for holding the reaction vessels. The plurality of processing track slots are disposed directly below the plurality of incubation track slots in vertical alignment.

In still another embodiment, a method of moving reaction vessels in a diagnostic analyzer is disclosed. In one step, an incubation track holding reaction vessels is moved. In another step, reagents are pipetted with a pipetting device from a reagent carousel to the reaction vessels held by the incubation track. In an additional step, the reaction vessels are transferred, using a reaction vessel exchanger device, from the incubation track to at least one processing track disposed below the incubation track. In yet another step, the reagents are pipetted with the pipetting device from the reagent carousel to the reaction vessels held by the at least one processing track.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

FIG. 9 illustrates a top perspective view of one embodiment of a reaction vessel moving device in a raised position which may be alternatively added into the embodiment of FIGS. 1-8 to move reaction vessels from the incubation track to the processing tracks;

FIG. 10 illustrates the same top perspective view of the embodiment of FIG. 9 of the reaction vessel moving device having been moved to a lowered position;

DETAILED DESCRIPTION

Figure 1:
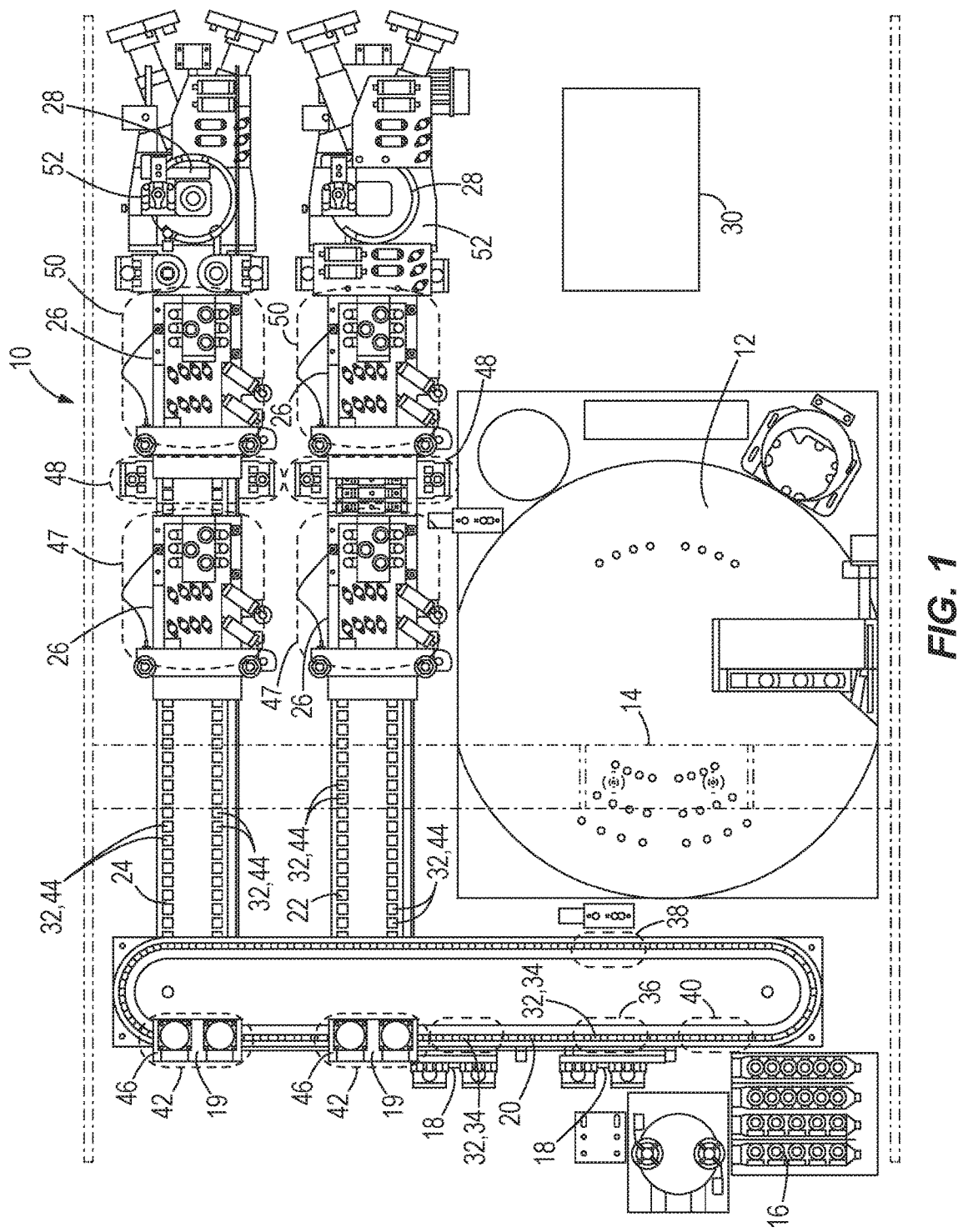
FIG. 1 illustrates a top view of one embodiment of a diagnostic analyzer.

FIG. 1 illustrates a top view of one embodiment of a diagnostic analyzer 10. In one embodiment, the diagnostic analyzer 10 in part comprises a reagent carousel 12 containing one or more reagents for a diagnostic test, a pipetting device 14, a sample supply device 16, reaction vessel supply devices 18, reaction vessel exchanger devices 19, an incubation track 20 defining a first sample processing path, processing tracks 22 and 24 defining second sample processing paths, wash devices 26, detection devices 28, and at least one processor 30.

The at least one processor 30 controls the reaction vessel supply devices 18 so that the supply devices 18 supply reaction vessels 32 into spaced-apart incubation track slots 34 of the incubation track 20 at locations 36. The reaction vessels 32 are operable to contain a sample and one or more reagents for carrying out a reaction for a diagnostic analysis. In the embodiment shown in FIG. 1, the at least one processor 30 then controls the incubation track 20 to move clockwise, causing the reaction vessels 32 residing in the incubation track 20 to advance the reaction vessels 32 to location 38. At location 38, the at least one processor 30 controls the pipetting device 14 to pipette reagent from the reagent carousel 12 into the reaction vessels 32 held by the incubation track 20. Subsequently, the at least one processor 30 controls the incubation track 20 to move clockwise to location 40. At location 40, the at least one processor 30 controls the pipetting device 14 to pipette samples from the sample supply device 16 into the reaction vessels 32 held by the incubation track 20. In one embodiment, the at least one processor 30 controls the incubation track 20 to move clockwise to locations 42. In another embodiment, the at least one processor 30 controls incubation track 20 to move clockwise to cause the reaction vessels 32 to move through locations 42, 38, 40 and 36 again to allow the sample and reagent in the reaction vessels 32 to incubate and complete a desired reaction. In this embodiment, the reaction vessels, do not undergo additional processes at locations 36 and 38. At locations 42, the at least one processor 30 controls the reaction vessel exchanger devices 19 to transfer the reaction vessels 32 from the incubation track slots 34 of the incubation track 20 into spaced-apart processing track slots 44 of the processing tracks 22 and 24 at locations 46 directly below the incubation track 20. It is noted that the processing tracks 22 and 24 are disposed below the incubation track 20 in perpendicular alignment. It is further noted that the plurality of processing track slots 44 of the processing tracks 22 and 24 are disposed below the plurality of incubation track slots 34 of the incubation track 20 in vertical alignment. In other embodiments, the configuration of the processing tracks 22 and 24 and the incubation track 20 may vary.

Subsequently, the at least one processor 30 controls the processing tracks 22 and 24 to advance the reaction vessels 32 held in the processing track slots 44 to wash devices 26 at location 47 at which point the samples contained in the reaction vessels 32 are washed. In one embodiment, the processing tracks 22 and 24 are formed as a continuous linear belt-like track that is disposed around pulleys. The pulleys may engage the processing tracks 22 and 24 in a sprocket-wheel engagement, in a friction engagement, or other forms of engagement to cause translation or movement of the processing tracks 22 and 24. In one embodiment, a motor supplies power to one or more of the pulleys in order to rotate the pulleys. The rotation of the pulleys causes the interfaced processing tracks 22 and 24 to rotate with and around the pulleys, thereby moving the processing tracks 22 and 24 simultaneously. Next, the at least one processor 30 controls the processing tracks 22 and 24 to advance the reaction vessels 32 held in the processing track slots 44 to location 48 at which point the at least one processor 30 controls the pipetting device 14 to pipette reagent from the reagent carousel 12 into the reaction vessels 32. Subsequently, the at least one processor 30 controls the processing tracks 22 and 24 to advance the reaction vessels 32 held in the processing track slots 44 to wash devices 26 at location 50 at which point the samples contained in the reaction vessels 32 are washed. During the washing, unbound materials of the reagents and sample are washed away from magnetically bound materials. Finally, the at least one processor 30 controls the processing tracks 22 and 24 to advance the reaction vessels 32 held in the processing track slots 44 to detection devices 28 at locations 52 at which point the detection devices 28 take readings of the samples contained in the reaction vessels 32.

Figure 2:
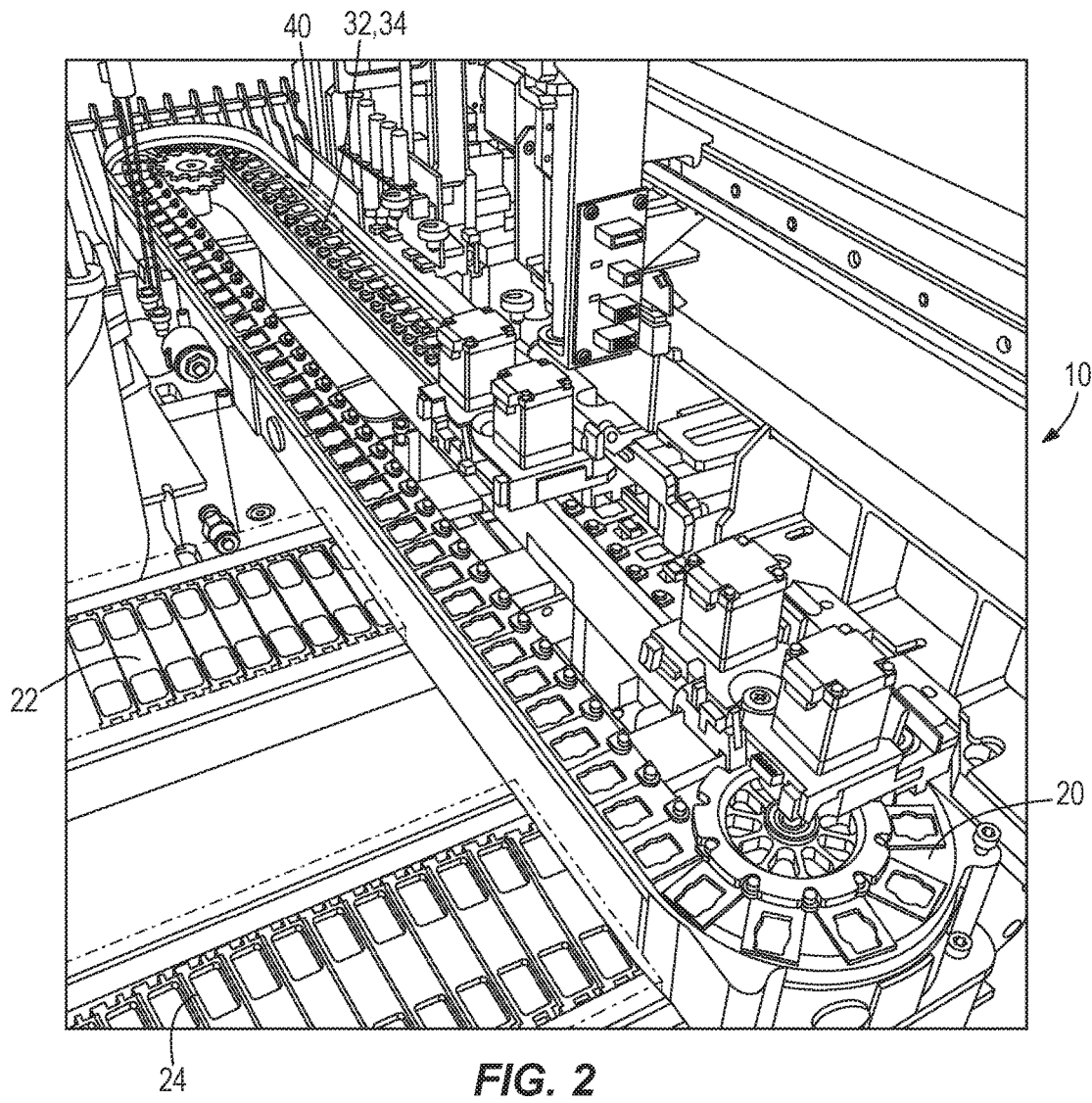
FIG. 2 illustrates a partial top perspective view of an incubation track and processing tracks of the diagnostic analyzer of the embodiment of FIG. 1 showing a reaction vessel in a first orientation located at one location within an incubation track slot of the incubation track.
Figure 3:
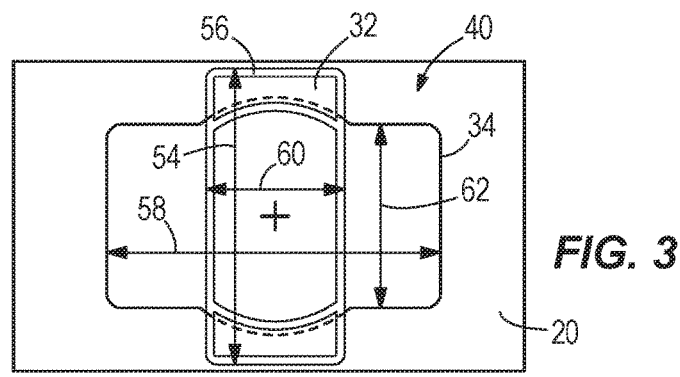
FIG. 3 illustrates a top view showing the first orientation of the reaction vessel at the location within the incubation track slot of the incubation track.

FIG. 2 illustrates a partial top perspective view of the incubation track 20 and the processing tracks 22 and 24 of the diagnostic analyzer 10 of the embodiment of FIG. 1 showing a reaction vessel 32 in a first orientation located at location 40 within an incubation track slot 34 of the incubation track 20 as described above. FIG. 3 illustrates a top view showing the first orientation of the reaction vessel 32 at location 40 within the incubation track slot 34 of the incubation track 20. It is noted that all of the reaction vessels 32 are oriented in this first orientation within and relative to the incubation track slots 34 from the time when they are supplied into the incubation track slots 34 at location 36 (shown in FIG. 1) up until the time they are delivered to location 42 (shown in FIG. 1) within the reaction vessel exchanger devices 19.

As shown in FIG. 3, when the reaction vessel 32 is disposed in the first orientation, the length 54 of the top ledge 56 of the reaction vessel 32 is disposed perpendicular to the length 58 of the incubation track slot 34 and the width 60 of the top ledge 56 of the reaction vessel 32 is disposed perpendicular to the width 62 of the incubation track slot 34. The length 54 of the top ledge 56 of the reaction vessel 32 is longer than the width 60 of the top ledge 56 of the reaction vessel 32. The length 58 of the incubation track slot 34 is greater than both the length 54 and the width 60 of the top ledge 56 of the reaction vessel 32. The width 62 of the incubation track slot 34 is larger than the width 60 of the top ledge 56 of the reaction vessel 32 but smaller than the length 54 of the top ledge 56 of the reaction vessel 32. When the reaction vessel 32 is disposed in the first orientation the reaction vessel 32 is held in place within the incubation track slot 34 of the incubation track 20 because the length 54 of the top ledge 56 of the reaction vessel 32 is greater than the width 62 of the incubation track slot 34. As a result, the top ledge 56 of the reaction vessel 32 rests in place on top of the incubation track slot 34 while a bottom portion (not shown) of the reaction vessel 32 is disposed through the incubation track slot 34 as a result of its size being smaller than the incubation track slot 34.

Figure 4:
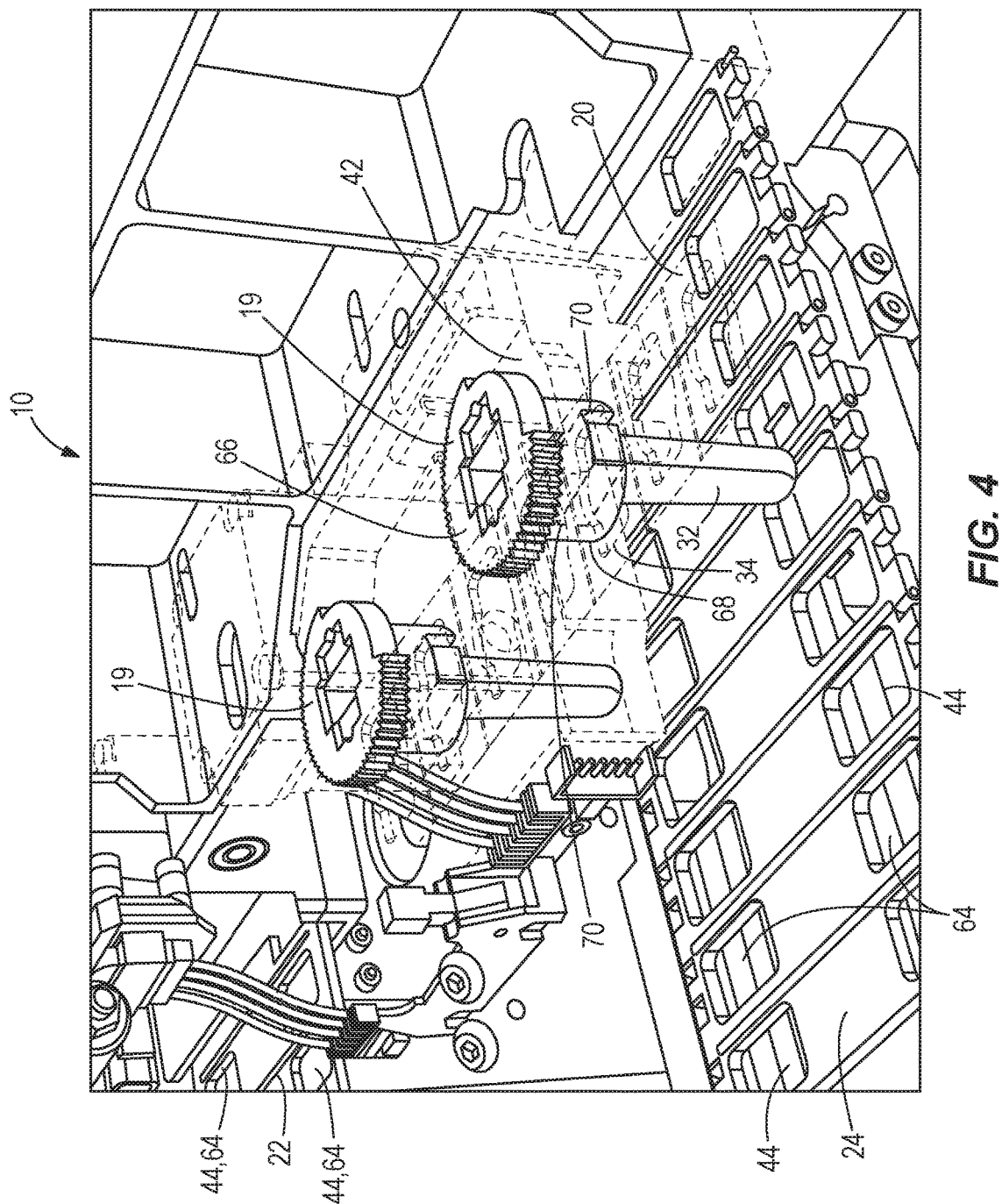
FIG. 4 illustrates a smaller top partial perspective view of the incubation track and processing tracks of the diagnostic analyzer of the embodiment of FIG. 2 showing the reaction vessel oriented in the first orientation within the incubation track slot of the incubation track at another location within a reaction vessel exchanger device.

FIG. 4 illustrates a smaller top partial perspective view of the incubation track 20 and processing tracks 22 and 24 of the diagnostic analyzer 10 of the embodiment of FIG. 2 showing the reaction vessel 32 oriented in the first orientation within the incubation track slot 34 of the incubation track 20 at location 42 within reaction vessel exchanger device 19. It is noted that there are two reaction vessel exchanger devices 19 located over each of the processing tracks 22 and 24. Each of the processing tracks 22 and 24 contain two lanes 64 of the processing track slots 44. A separate reaction vessel exchanger device 19 is located over each lane 64 of the processing track slots 44 of each of the processing tracks 22 and 24 (see also FIG. 1). Each of the separate reaction vessel exchanger devices 19 are configured to transfer reaction vessels 32, one at a time, from the incubation track slots 34 of the incubation track 20 to its assigned lane 64 of processing track slots 44.

Each reaction vessel exchanger device 19 comprises a rotation member 66 to rotate a reaction vessel 32, as it is held by an incubation track slot 34 of the incubation track 20, from the first orientation to a second orientation. The rotation member 66 comprises an open-ended shaft 68 having opposed slots 70. The opposed slots 70 are sized to allow the reaction vessels 32 to pass through the opposed slots 70. When the incubation track 20 moves a reaction vessel 32 to location 42 the reaction vessel 32 passes through one of the opposed slots 70 into the open-ended shaft 68 of the rotation member 66 between the opposed slots 70.

Figure 5:
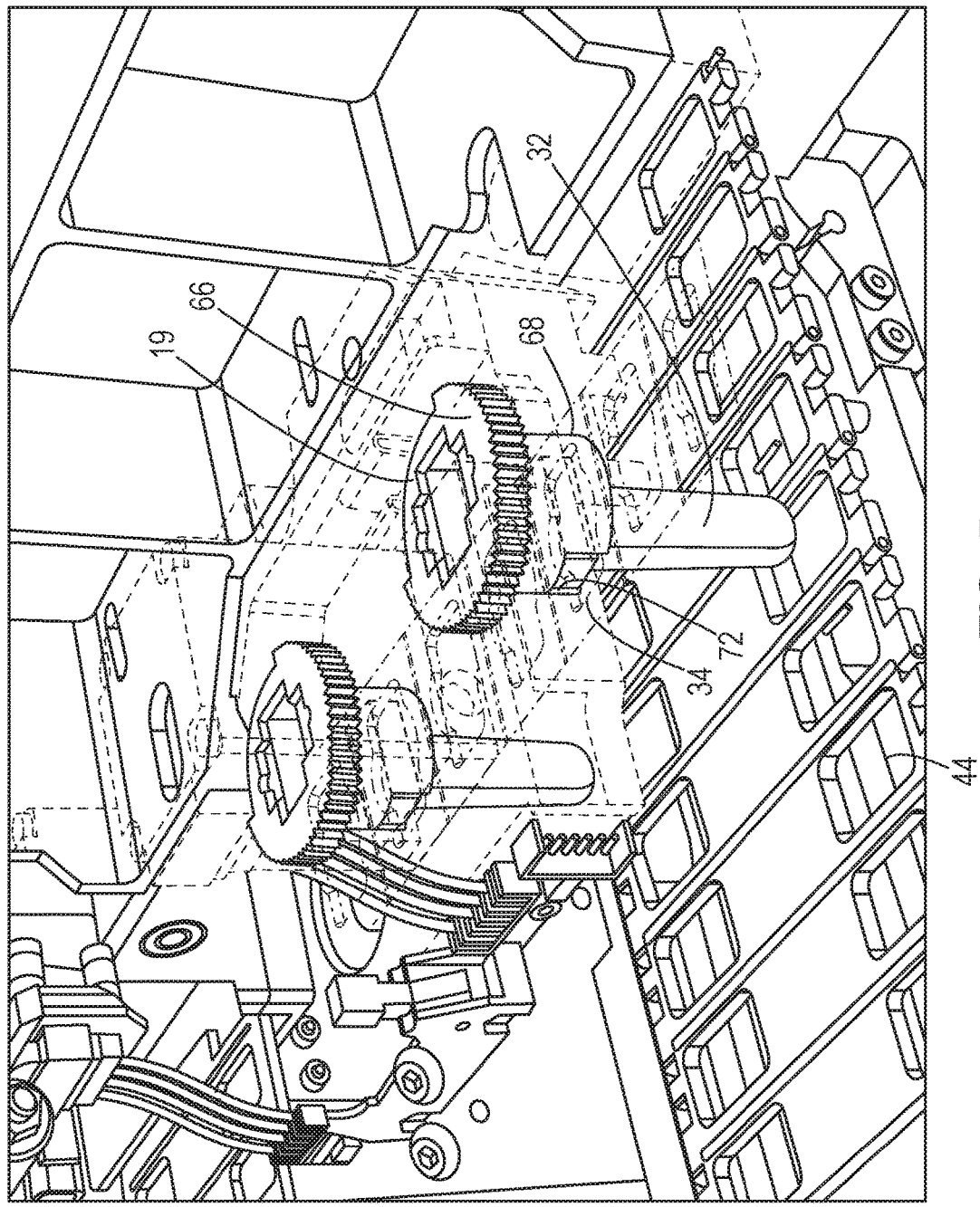
FIG. 5 illustrates the same top partial perspective view of the embodiment of FIG. 4 with a rotation member of the reaction vessel exchanger device having rotated ninety degrees to rotate the reaction vessel ninety degrees from the first orientation of FIG. 4 to a second orientation of FIG. 5.

FIG. 5 illustrates the same top partial perspective view of the embodiment of FIG. 4 with the rotation member 66 of the reaction vessel exchanger device 19 having rotated ninety degrees to rotate the reaction vessel 32 ninety degrees from the first orientation of FIG. 4 to the second orientation of FIG. 5. The at least one processor 30 (shown in FIG. 1) caused the rotation member 66 of the reaction vessel exchanger device 19 to rotate. During this rotation, an inner shaft wall 72 of the opened-ended shaft 68 abutted against the reaction vessel 32 forcing it to rotate with the rotation member 66 from the first orientation of FIG. 4 to the second orientation of FIG. 5.

Figure 6:
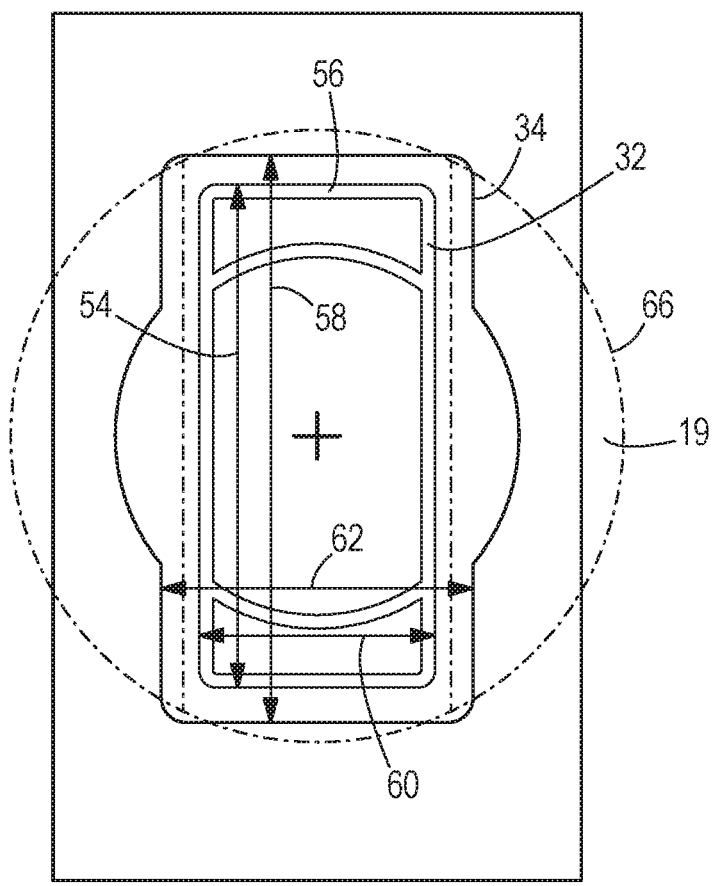
FIG. 6 illustrates a top view showing the second orientation of the reaction vessel disposed within the incubation track slot within the rotation member of the reaction vessel exchanger device.

FIG. 6 illustrates a top view showing the second orientation of the reaction vessel 32 disposed within the incubation track slot 34 within the rotation member 66 of the reaction vessel exchanger device 19. As shown in FIG. 6, when the reaction vessel 32 is disposed in the second orientation the length 54 of the top ledge 56 of the reaction vessel 32 is disposed parallel to the length 58 of the incubation track slot 34 and the width 60 of the top ledge 56 of the reaction vessel 32 is disposed parallel to the width 62 of the incubation track slot 34. Because the length 58 of the incubation track slot 34 is greater than the length 54 of the top ledge 56 of the reaction vessel 32 and the width 62 of the incubation track slot 34 is greater than the width 60 of the top ledge 56 of the reaction vessel 32, the reaction vessel 32 may pass through the incubation track slot 34 towards the processing track slot 44 (shown in FIG. 5) which is disposed in vertical alignment directly below the incubation track slot 34. In one embodiment, the reaction vessel 32 is passed through the incubation track slot 34 towards the processing track slot 44 by falling through the incubation track slot 34 by gravitational force.

Figure 7:
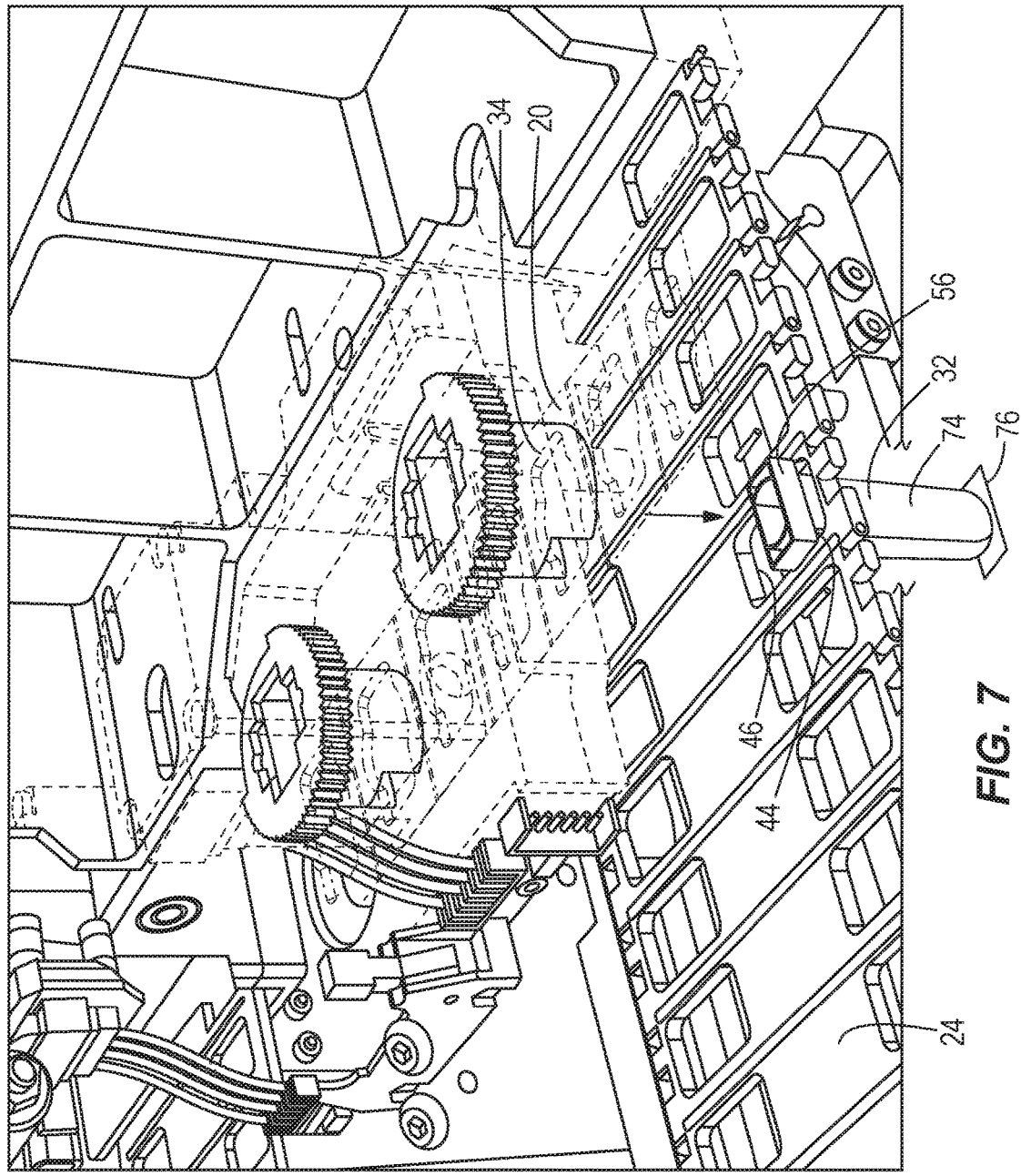
FIG. 7 illustrates the same top partial perspective view of the embodiment of FIG. 5 with the reaction vessel having fallen through the incubation track slot of the incubation track into the processing track slot of the processing track at another location.

FIG. 7 illustrates the same top partial perspective view of the embodiment of FIG. 5 with the reaction vessel 32 having passed through the incubation track slot 34 of the incubation track 20 into the processing track slot 44 of the processing track 24 at location 46. The reaction vessel 32 has retained its second orientation and has landed within the processing track slot 44 with the size of the processing track slot 44 configured to hold the top ledge 56 of the reaction vessel 32 in place and prevent the top ledge 56 of the reaction vessel 32 from falling through the processing track slot 44. The bottom portion 74 of the reaction vessel 32 is disposed through the processing track slot 44 as a result of its size being smaller than the processing track slot 44. In one embodiment, the fall of the bottom portion 74 of the reaction vessel 32 through the processing track slot 44 was dampened by a dampening device 76 disposed below the processing track slot 44 to reduce splashing of the sample and reagents contained within the reaction vessel 32. In one embodiment, the dampening device 76 comprises a pillow. In other embodiments, the dampening device 76 may comprise a spring, a flexible member or any other type of dampening device for dampening the fall of the reaction vessel 32 through the processing track slot 44.

Figure 7A:
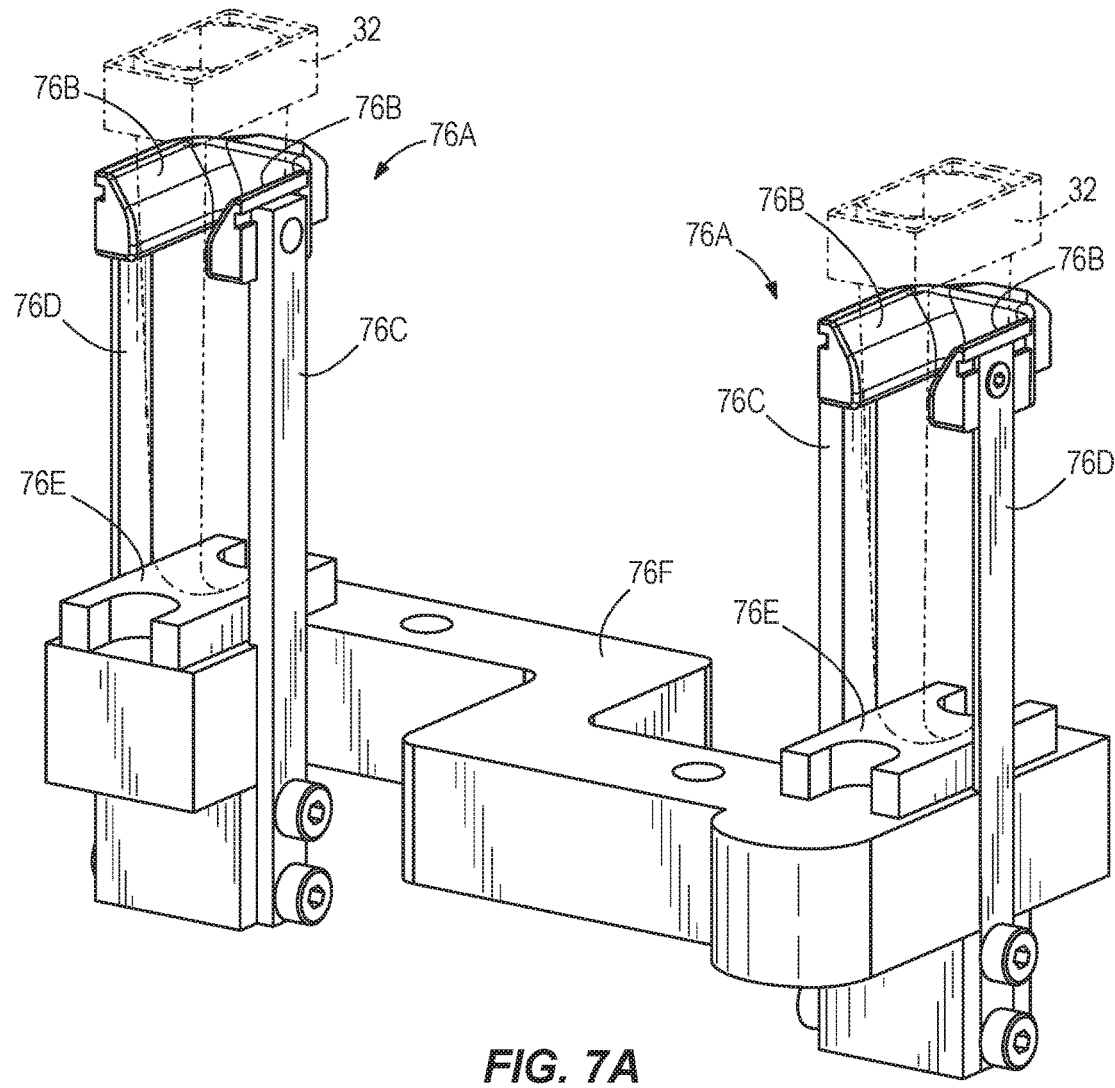
FIG. 7A illustrates a perspective view of an embodiment of a dampening device which may be used in the embodiment of FIG. 7 to reduce splashing of sample and reagents within the reaction vessel as they fall through the incubation track slot of the incubation track into the processing track slot of the processing track.

FIG. 7A illustrates a perspective view of another embodiment of a dampening device 76A. The dampening device 76A may replace the dampening device 76 of FIG. 7 to further reduce or eliminate splashing of the sample and reagents contained within the reaction vessel 32. The dampening device 76A comprises low friction guides 76B, support members 76C, damping springs 76D, pads 76E, and base 76F. The low friction guides 76B are sized to apply a small amount of friction on the reaction vessels 32 as the reaction vessels 32 slide through the low friction guides 76B to reduce the amount of impact when the reaction vessels 32 contact the pads 76E thereby reducing splashing of the sample and reagents within the reaction vessels 32. The support members 76C are attached to and fixed in place between the low friction guides 76B and the base 76F holding the low friction guides 76B above the base 76F. The damping springs 76D are also attached to and fixed in place between the low friction guides 76B and the base 76F holding the low friction guides 76B above the base 76F. The damping springs 76D are made of a spring like material to provide some springiness to the low friction guides 76B. The pads 76E are made of a flexible material such as rubber. In other embodiments, the configuration, size, shape, orientation, and material of the dampening device 76A may vary.

Figure 7B:
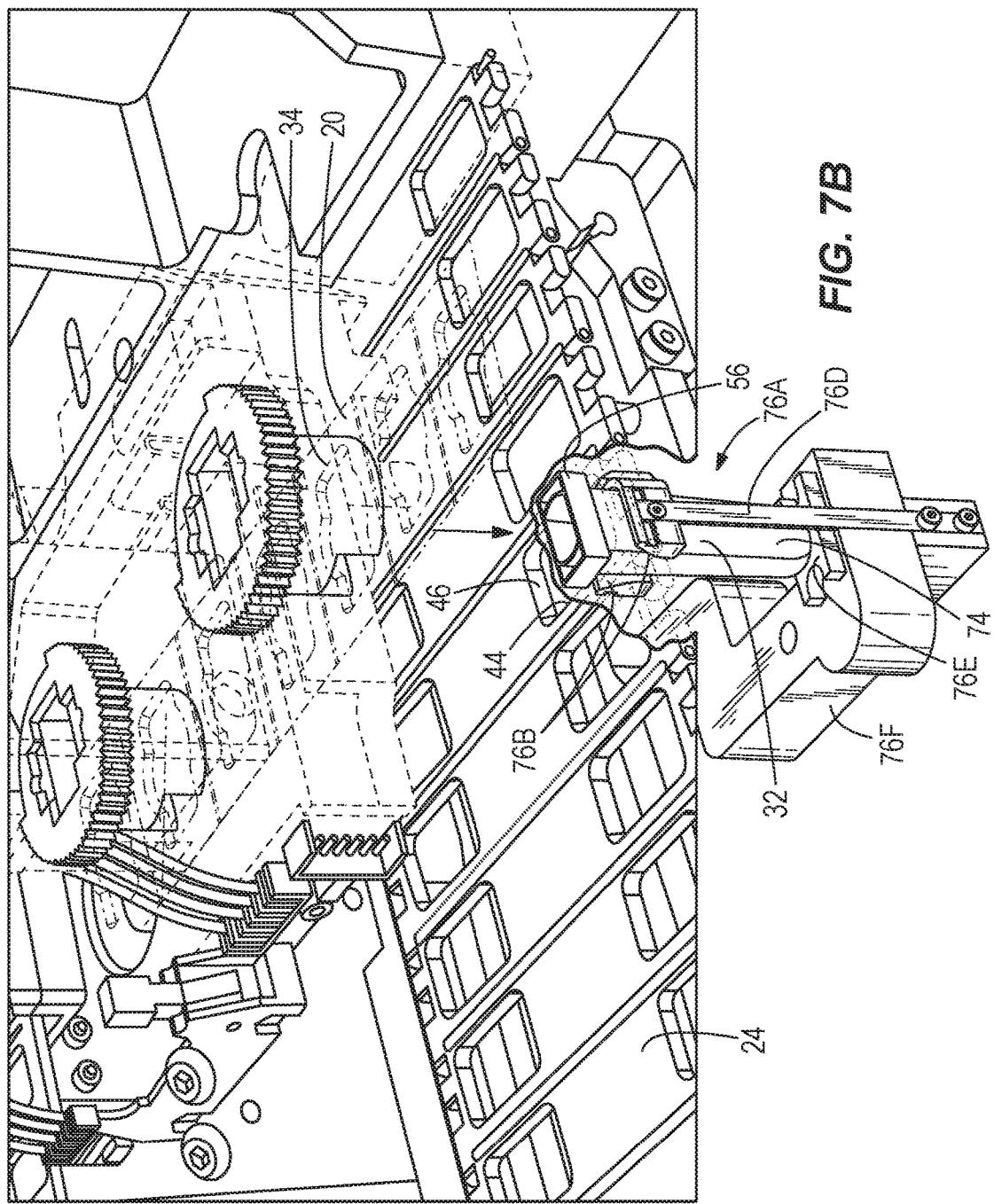
FIG. 7B illustrates the same top partial perspective view of the embodiment of FIG. 7 with the only difference being that the dampening device of FIG. 7A has replaced a dampening device of FIG. 7.

FIG. 7B illustrates the same top partial perspective view of the embodiment of FIG. 7 with the only difference being that the dampening device 76A of FIG. 7A has replaced the dampening device 76 of FIG. 7. As shown, the reaction vessel 32 has passed through the incubation track slot 34 of the incubation track 20 into the processing track slot 44 of the processing track 24 at location 46. The reaction vessel 32 has retained its second orientation and has landed within the processing track slot 44 with the size of the processing track slot 44 configured to hold the top ledge 56 of the reaction vessel 32 in place and prevent the top ledge 56 of the reaction vessel 32 from falling through the processing track slot 44. The bottom portion 74 of the reaction vessel 32 is disposed through the processing track slot 44 as a result of its size being smaller than the processing track slot 44. The fall of the bottom portion 74 of the reaction vessel 32 through the processing track slot 44 was dampened by the dampening device 76A disposed below the processing track slot 44 to reduce splashing of the sample and reagents contained within the reaction vessel 32. The low friction guides 76B applied a small amount of friction on the reaction vessel 32 as the reaction vessel 32 slid through the low friction guide 76B thereby reducing the amount of impact when the reaction vessel 32 contacted the pad 76E and in-turn reducing splashing of the sample and reagents within the reaction vessel 32.

Figure 8:
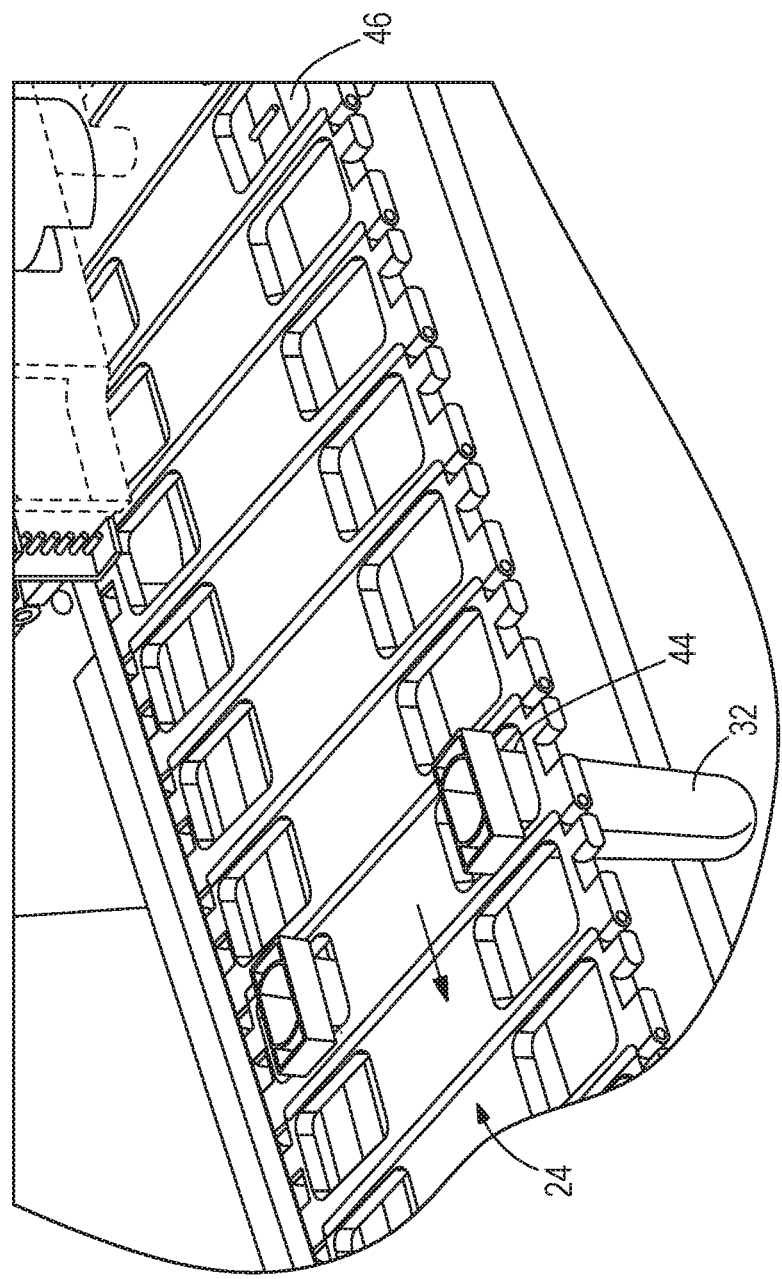
FIG. 8 illustrates a smaller top partial perspective view of the processing track of the embodiment of FIG. 7 being moved counter-clockwise to move the reaction vessel oriented in the second position in the processing track slot to still another location at a wash device.

FIG. 8 illustrates a smaller top partial perspective view of the processing track 24 of the embodiment of FIG. 7 being moved counter-clockwise, as controlled by the at least one processor 30 (shown in FIG. 1), to move the reaction vessel 32 oriented in the second position in the processing track slot 44 from location 46 towards the wash device 26 (shown in FIG. 1) located at location 47 (shown in FIG. 1). As previously discussed with respect to FIG. 1, after the wash device 26 washes the sample contained in the reaction vessel 32 at location 47, the at least one processor 30 controls the processing track 24 to move the processing track 24 to advance the reaction vessel 32 oriented in the second position in the processing track slot from location 47 to location 48 at which point the at least one processor 30 controls the pipetting device 14 to pipette reagent from the reagent carousel 12 into the reaction vessel 32. As previously discussed with respect to FIG. 1, after the pipetting device 14 pipettes reagent into the reaction vessel 32 at location 48, the at least one processor 30 controls the processing track 24 to move it counter-clockwise to move the reaction vessel 32 oriented in the second position in the processing track slot 44 to the wash device 26 at location 50. As previously discussed with respect to FIG. 1, after the wash device 26 washes the sample contained in the reaction vessel 32 at location 50, the at least one processor 30 controls the processing track 24 to move it counter-clockwise to move the reaction vessel 32 oriented in the second position in the processing track slot 44 from location 50 to location 52 at which point the detection device 28 takes a reading of the sample contained in the reaction vessel 32.

Although FIGS. 2-8 only show the movement of one reaction vessel 32 between the various locations, it is noted that all of the reaction vessels 32 are moved in the same manner between the various locations assisted by the reaction vessel exchanger devices 19 transferring the reaction vessels 32 from the incubation track 20 to the lanes 64 of the processing tracks 22 and 24 as discussed above with respect to FIG. 4. In other embodiments, the components of the diagnostic analyzer 10 may vary, the components of the diagnostic analyzer 10 may be oriented or configured in different locations, or one or more additional components may be added to the diagnostic analyzer 10.

FIG. 9 illustrates a top perspective view of one embodiment of a reaction vessel moving device 80 in a raised position which may be alternatively added into the embodiment of FIGS. 1-8 to engage and move reaction vessels 32 from the incubation track 20 to the processing tracks 22 and 24 to avoid or limit splashing of the sample and reagents within the reaction vessels 32. The reaction vessel moving device 80 comprises a motor 82, a shaft 84, a plate 86, a linear guide 88, posts 90, moving devices 92, and screws or bearings 94. The motor 82 is configured to raise and lower the shaft 84 and the attached plate 86. Since the plate 86 is attached to the posts 90 which are attached to the moving devices 92, this movement also raises and lowers these components. The linear guide 88 forces the components to travel linearly in a vertical up and down direction. The screws or bearings 94 allow the moving devices 92 to rotate. In one embodiment, the moving devices 92 comprise tulip shapes made of a flexible, elastomeric material which are sized and shaped to fit over and latch onto a reaction vessel 32 (collectively shown in FIGS. 1-8) when the moving devices 92 are located in the raised position of FIG. 9 and to release the reaction vessel 32 when the moving devices 92 are lowered to the lowered position of FIG. 10. In other embodiments, the moving devices 92 may vary in shape, size, configuration, orientation, and material. For instance, in another embodiment the moving devices 92 may be configured, sized, and shaped to merely contact and support the reaction vessel 32 in the raised position of FIG. 9, without latching onto the reaction vessel 32, and may move the reaction vessel 32 to the lowered position of FIG. 10

Figure 12:
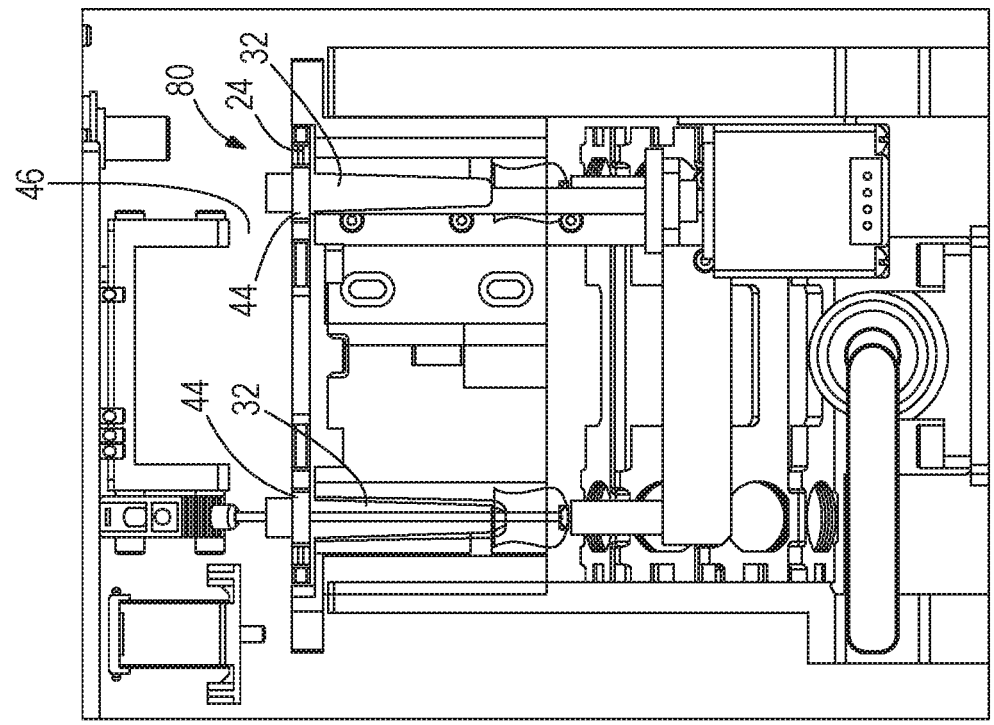
FIG. 12 illustrates the same side cross-section view of the reaction vessel moving device of the embodiment of FIG. 11 in a lowered position having released the reaction vessels after the reaction vessels were disposed in the processing track slots of the processing track at another location.
Figure 11:
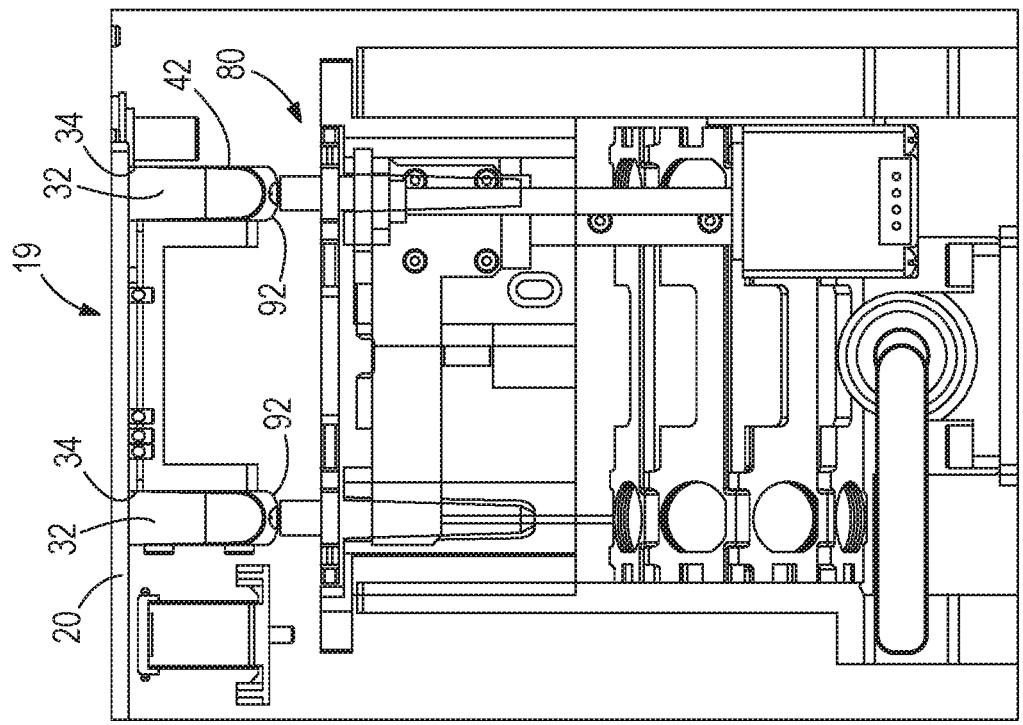
FIG. 11 illustrates a side cross-section view of the reaction vessel moving device of the embodiment of FIG. 9 in a raised position contacting and supporting the reaction vessels as they are disposed in incubation track slots of the incubation track within the reaction vessel exchanger device at one location.

FIG. 10 illustrates the same top perspective view of the embodiment of FIG. 9 of the reaction vessel moving device 80 having been moved to a lowered position. FIG. 11 illustrates a side cross-section view of the reaction vessel moving device 80 of the embodiment of FIG. 9 in a raised position engaging the reaction vessels 32 at location 42 as they are disposed in incubation track slots 34 of the incubation track 20 within the reaction vessel exchanger device 19. As the reaction vessel exchanger device 19 rotates the reaction vessels 32 from their first position to their second position the moving devices 92 rotate with the reaction vessels 32 which are disposed within the moving devices 92. FIG. 12 illustrates the same side cross-section view of the reaction vessel moving device 80 of the embodiment of FIG. 11 in a lowered position having released the reaction vessels 32 after the reaction vessels 32 were disposed in the processing track slots 44 of the processing track 24 at location 46. In other embodiments, the reaction vessel moving device 80 may vary in size, configuration, orientation, location, material, or function.

Figure 13:
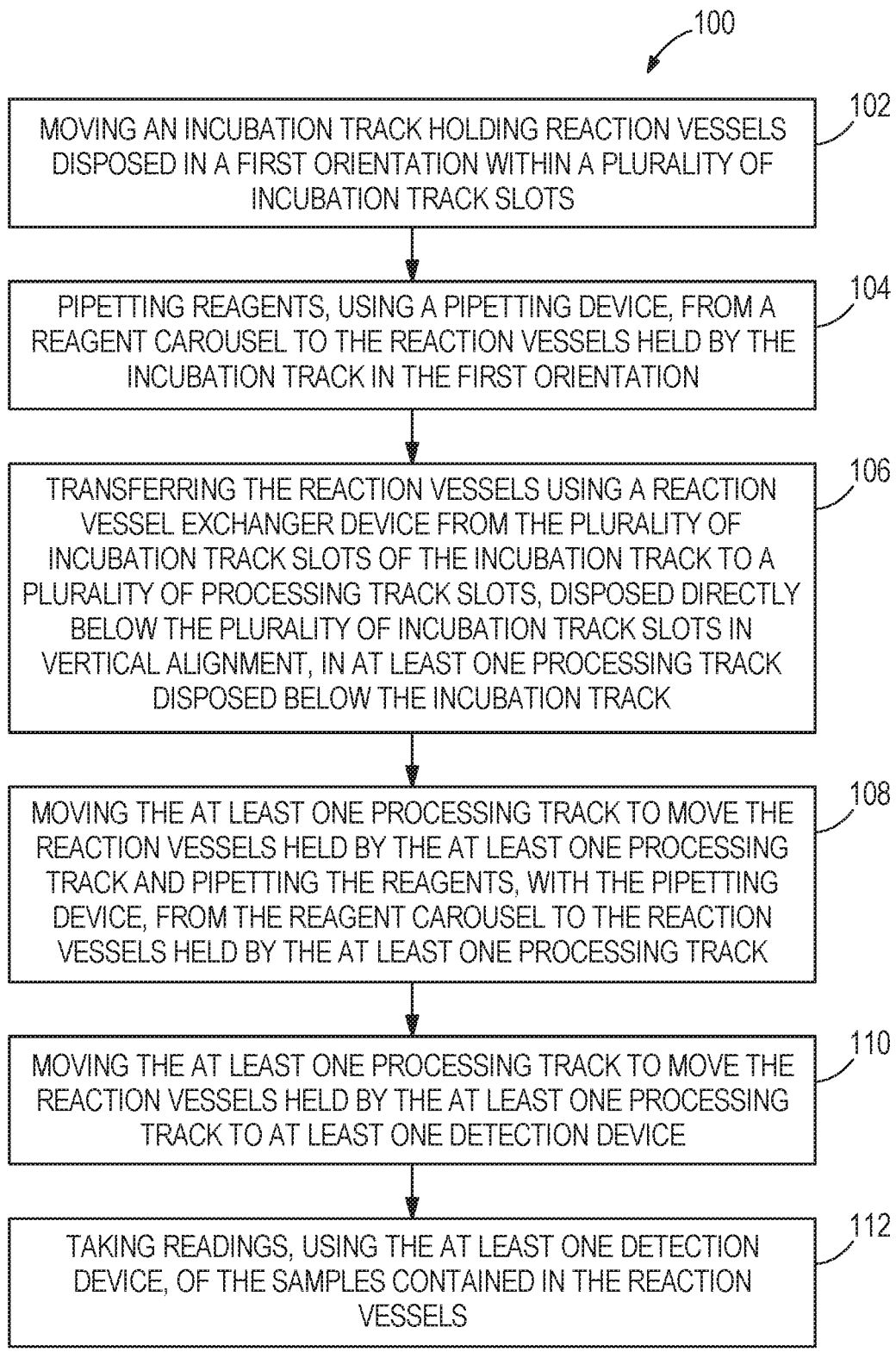
FIG. 13 is a flowchart illustrating one embodiment of a method of moving reaction vessels in a diagnostic analyzer.

FIG. 13 is a flowchart illustrating one embodiment of a method 100 of moving reaction vessels in a diagnostic analyzer. The method 100 may utilize any of the diagnostic analyzers disclosed herein. In other embodiments, the method 100 may utilize varying diagnostic analyzers. In step 102, an incubation track holding reaction vessels disposed in a first orientation within a plurality of incubation track slots is moved. In step 104, reagents are pipetted, using a pipetting device, from a reagent carousel to the reaction vessels held by the incubation track in the first orientation. In step 106, the reaction vessels are transferred using a reaction vessel exchanger device from the plurality of incubation track slots of the incubation track to a plurality of processing track slots, disposed directly below the plurality of incubation track slots in vertical alignment, in at least one processing track disposed below the incubation track.

In one embodiment, step 106 comprises the reaction vessels passing through a slot of an open-ended shaft and an inner shaft wall of an open-ended shaft of a rotation member abutting against the reaction vessels to rotate the reaction vessels from the first orientation within the incubation track slots to a second orientation within the incubation track slots so that the reaction vessels pass through the incubation track slots into the processing track slots. In another embodiment, step 106 comprises gravity causing the reaction vessels to pass through the plurality of incubation track slots of the incubation track into the processing track slots of the processing tracks. In yet another embodiment, step 106 comprises a reaction vessel moving device contacting and supporting the reaction vessels and moving the reaction vessels through the incubation track slots into the processing track slots. The reaction vessel moving device may comprise a flexible member fitting over and against the reaction vessels. In other embodiments, the reaction vessel moving device may vary in form and function. In still another embodiment, step 106 comprises dampening movement of the reaction vessels as they move into the processing track slots with a dampening device disposed below the processing track slots. The dampening device may comprise a pillow, a flexible member such as a spring, a low friction guide, or another type of dampening member.

In step 108, the at least one processing track is moved to move the reaction vessels held by the at least one processing track and the reagents are pipetted, with the pipetting device, from the reagent carousel to the reaction vessels held by the at least one processing track. In step 110, the at least one processing track is moved to move the reaction vessels held by the at least one processing track to at least one detection device. In step 112, readings are taken, using the at least one detection device, of the samples contained in the reaction vessels. In still other embodiments, one or more steps of the method 100 may be varied in substance or order, one or more steps may not be followed, or one or more steps may be added.

One or more embodiments of the disclosure reduces cost and maintenance, and saves space over one or more of the existing diagnostic analyzers due to the use of the shared pipetting device and reagent carousel, and the use of the efficient reaction vessel exchanger device to transfer reaction vessels. Still other issues associated with one or more additional existing diagnostic analyzers may be reduced or overcome using one or more embodiments of the disclosure.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. Furthermore, it is to be understood that the disclosure is defined by the appended claims. Accordingly, the disclosure is not to be restricted except in light of the appended claims and their equivalents.

The invention claimed is:

1. A diagnostic analyzer comprising:
a first sample process path having an incubation track operable to move reaction vessels along the first sample process path;
a second sample process path having a processing track disposed below the first sample process path and operable to move reaction vessels along the second sample process path;
a reaction vessel exchanger device operable to transfer the reaction vessels from the first sample process path to the second sample process path;
a pipetting device operable to pipette reagents or samples into the reaction vessels held by the incubation track; and
at least one detection device operable to take readings of the samples contained in the reaction vessels;
wherein the reaction vessel exchanger device comprises a rotation member operable to rotate the reaction vessels, as they are held by the incubation track, from a first orientation to a second orientation; the incubation track comprises a plurality of incubation track slots operable to hold the reaction vessels, and the processing track comprises a plurality of processing track slots operable to hold the reaction vessels, the plurality of processing track slots disposed directly below the plurality of incubation track slots in vertical alignment; and the incubation track slots and the reaction vessels are sized so that when the reaction vessels are disposed in the first orientation within the incubation track slots the reaction vessels will be held by the incubation track, and when the reaction vessels are disposed in the second orientation within the incubation track slots the reaction vessels will pass through the incubation track slots into the processing track slots.

2. The diagnostic analyzer of claim 1 wherein the processing track is operable to move the reaction vessels, with the samples disposed in them, to the at least one detection device.

3. The diagnostic analyzer of claim 1 wherein the incubation track and the processing track each separately comprise a continuous linear belt-like track disposed around pulleys.

4. The diagnostic analyzer of claim 3 wherein a first longitudinal axis of the first sample process path is disposed perpendicular to a second longitudinal axis of the second sample process path.

5. The diagnostic analyzer of claim 1 wherein the rotation member comprises an open-ended shaft having opposed slots, the opposed slots sized to allow the reaction vessels to pass through the opposed slots, an inner shaft wall of the open-ended shaft being sized to abut against the reaction vessels.

6. The diagnostic analyzer of claim 1 wherein the reaction vessel exchanger device further comprises a reaction vessel moving device operable to contact and support the reaction vessels and move them through the incubation track slots into the processing track slots.

7. The diagnostic analyzer of claim 6 wherein the reaction vessel moving device comprises a flexible member sized to fit over and against the reaction vessels.

8. The diagnostic analyzer of claim 1 further comprising a dampening device disposed below the processing track slots which is operable to dampen movement of the reaction vessels as they move into the processing track slots.

\* \* \* \* \*